(12) United States Patent
Cao et al.

(10) Patent No.: US 9,005,678 B1
(45) Date of Patent: Apr. 14, 2015

(54) PHARMACEUTICAL COMPOSITION FOR TREATING CANCER AND USE THEREOF

(71) Applicant: Jiangsu Province Institute of Traditional Chinese Medicine, Nanjing, Jiangsu (CN)

(72) Inventors: Peng Cao, Jiangsu (CN); Xiaolan Cheng, Jiangsu (CN); Jiege Huo, Jiangsu (CN); Xiaoning Wang, Jiangsu (CN); Jingqing Hu, Jiangsu (CN); Xueting Cai, Jiangsu (CN); Yang Yang, Jiangsu (CN); Chunping Hu, Jiangsu (CN); Guoli Wei, Jiangsu (CN)

(73) Assignee: Jiangsu Province Institute of Traditional Chinese Medicine, Nanjing, Jiangsu (CN)

( * ) Notice: Subject to any disclaimer, the term of this patent is extended or adjusted under 35 U.S.C. 154(b) by 0 days.

(21) Appl. No.: 14/250,914

(22) Filed: Apr. 11, 2014

(30) Foreign Application Priority Data

Nov. 26, 2013 (CN) .......................... 2013 1 0611137

(51) Int. Cl.
| | | |
|---|---|---|
| *A01N 65/00* | (2009.01) | |
| *A61K 36/9068* | (2006.01) | |
| *A61K 31/555* | (2006.01) | |
| *A61K 36/481* | (2006.01) | |
| *A61K 36/54* | (2006.01) | |
| *A61K 36/65* | (2006.01) | |
| *A61K 36/725* | (2006.01) | |

(52) U.S. Cl.
CPC ........... *A61K 36/9068* (2013.01); *A61K 31/555* (2013.01); *A61K 36/481* (2013.01); *A61K 36/54* (2013.01); *A61K 36/65* (2013.01); *A61K 36/725* (2013.01)

(58) Field of Classification Search
CPC .................................................... A61K 36/906
USPC .......................................... 424/725, 739, 756
See application file for complete search history.

(56) References Cited

PUBLICATIONS

Jemal A, Bray F, Center MM, Ferlay J, Ward E, et al. Global Cancer Statistics. Cancer J Clin. 2011, 61: 69-90.
Park SB, Goldstein D, Krishnan AV, Lin CS, Friedlander ML, et al. Chemotherapy-induced peripheral neurotoxicity: A critical analysis. CA Cancer J Clin. 2013, doi: 10.1002/caac.21204.
Lavoie Smith EM, Li L, Hutchinson RJ, Ho R, Burnette WB, et al. Measuring vincristine-induced peripheral neuropathy in children with acute lymphoblastic leukemia. Cancer Nurs. 2013, 36: 49-60.
Argyriou AA, Polychronopoulos P, Iconomou G, Chroni E, Kalofonos HP. A review on oxaliplatin-induced peripheral nerve damage. Cancer Treat Rev 2008, 34: 368-377.
Scripture CD, Figg WD, Sparreboom A, Peripheral Neuropathy Induced Paclitaxel: Recent Insights and Future Perspectives. Curr Neurophamacol. 2006, 4, 165-172.
Leandro-García LJ, Leskelä S, Jara C, Gréen H, Avall-Lundqvist E, et al. Regulatory polymorphisms in β-tubulin IIa are associated with paclitaxel-induced peripheral neuropathy. Clin Cancer Res. 2012, 18: 4441-4448.
Cersosimo RJ. Oxaliplatin-associated neuropathy: a review. Ann Pharmacother. 2005, 39: 128-135.
Joseph EK, Chen X, Bogen O, Levin JD. Oxaliplatin acts on IB4-postive nociceptors to induce an oxidative stress-dependent acute painful peripheral neuropathy. J Pain 2008, 9: 463-372.
Scuteri A, Galimberti A, Ravasi M, Pasini S, Donzelli E, et al. NGF protects dorsal root ganglion neurons from oxaliplatin by modulating JNK/Sapk and ERK1/2. Neurosci Lett 2010, 486: 141-145.
Donzelli E, Carfi M, Miloso M, Strada A. Galbiati S, Bayssas M, Griffon-Etienne G, Cavaletti G, Petruccioli MG, Tredici G, Neurotoxicity of platinum compounds: Comparison of the effects of cisplatin and oxaliplatin on the human neuroblastoma cell line SH-SY5Y, J Neurooncol 2004, 67: 65-73.
Ta LE, Espeset L, Podratz J, Windebank AJ. Neurotoxicity of oxaliplatin and cisplatin for dorsal root ganglion neurons correlates with platinum-DNA binding. Neurotoxicology, 2006, 27. 992-1002.
Cavaletti G, Tredici G, Petruccioli MG, Dondè E, Tredici P, Marmiroli P, Minoia C, Ronchi A, Bayssas M, Etienne CG. Effects of different schedules of oxaliplatin treatment on the peripheral nervous system of the rat. Eur J Cancer 2001; 37: 2457-2463.
Jamieson SM, Liu J, Connor B, McKeage ML: Oxaliplatin causes selective atrophy of a subpopulation of dorsal root ganglion neurons without inducing cell loss. Cancer Chemother Pharmacol. 2005: 56: 391-399.
Renn CL, Carozzi VA, Rhee P, Gallop D, Dorsey SC, Cavaletti G. Multimodal assessment of painful peripheral neuropathy induced by chronic oxaliplatin-based chemotherapy in mice. Mol Pain, 2011, 7:29.
Weickhardt A, Wells K, Messersmith W. Oxaliplatin-induced Neuropathy in Colorectal Cancer. J Oncology, 2011, 2011: 201593.
Hoffman KR. Potential prevention and treatment of oxaliplatin associated peripheral neuropathy. J Clin Oncol. 2004, 22: 8093.
Cascinu S, Catalano V, Cordella L, Labianca R, Giordani P, et al. Neuroprotective Effect of Reduced Glutathione on Oxaliplatin-Based Chemotherapy in Advanced Colorectal Cancer: A Randomized, Double-Blind, Placebo-Controlled Trial, J Clin Oncol. 2002, 20: 3478-3483.
Wen F, Zhou Y, Wang W, Hu QC, Liu YT. Ca/Mg infusions for the prevention of oxaliplatin-related neurotoxicity in patients with colorectal cancer: a meta-analysis. Ann Oncol. 2012, 00: 1-8.
Grothey A, Nikcevich DA, Sloan JA, Kugler JW, Silberstein PT. Intravenous Calcium and Magnesium for Oxaliplatin-Induced Sensory Neurotoxicity in Adjuvant Colon Cancer. NCCTG N0407. J Clin Oncol. 2011, 29: 421-427.
Chaplan SR, Bach FW, Pogrel JW, Chung JM, Yaksh TL. Quantitative assessment of tactile allodynia in the rat paw. Journal of Neuroscience Methods 53 (1994) 53-63.

*Primary Examiner* — Michael Meller
(74) *Attorney, Agent, or Firm* — Rankin Hill & Clark LLP

(57) ABSTRACT

The present invention discloses a pharmaceutical composition for treating cancer, comprising: (1) a herbal composition generated from *Astragali membranaceus* radix, *Cinnamomi cortex, Paeonia alba* radix, *Jujubae fructus*, and *Zingiberis rhizoma* or an extract of the above mixed herbal medicine; (2) one or more chemotherapeutic compounds. The present invention also discloses use of the above pharmaceutical composition in the preparation of medicament for treating human cancer and in the preparation of medicament for reducing side effects of chemotherapeutic compounds in human body. The pharmaceutical composition of the present invention can reduce chemotherapy-induced peripheral neuropathic side effects such as limb paresthesia, pain, cold skin, formication, powerlessness and the like, increase tolerance dosages of anticancer drugs, and enhance efficacy of anticancer drugs.

1 Claim, 4 Drawing Sheets

PHARMACEUTICAL COMPOSITION FOR TREATING CANCER AND USE THEREOF

FIELD OF THE INVENTION

The present invention relates to a pharmaceutical composition for treating cancer and use thereof, belonging to the technical field of Chinese herbal medicine.

BACKGROUND OF THE INVENTION

In recent years, cancer has become the second leading cause of death after cardiovascular disease[1]. The treatments used for cancer mainly include surgery, radiotherapy and chemotherapy, and chemotherapy has become an important and essential strategy for cancer therapy by effecting different stages of tumor cell proliferation. However, several chemotherapeutic drugs are neurotoxic and can lead to chemotherapy-induced peripheral neuropathy (CIPN), a nerve disorder that can cause weakness, numbness, tingling and pain. CIPN is a major dose-limiting adverse effect of many anti-cancer drugs such as platinum salts (cisplatin, carboplatin and oxaliplatin), spindle poisons (taxanes and vinca alkaloids), bortezomib and thalidomide, and a potential reason to terminate or suspend chemotherapy, in some cases leading to disease progression[2-5]. For patients with CIPN symptoms, dose reduction or cessation of chemotherapy is not an effective solution, contrarily, it will make it difficult to manage cancer treatment, but not necessarily eliminate the neurotoxicity.

Up to date, the pathogenesis of CIPN has not been fully elucidated. It has been reported that the mechanism of peripheral neuropathy induced by taxol may be related to that axonal microtubule-associated protein makes axonal transport impaired[6]. Oxaliplatin-induced peripheral neuropathy may be caused by the chelation of calcium which can interfere with sodium ions-gated channels. According to the clinical research carried out by the National Cancer Institute and the World Health Organization, 15% of cancer patients treated with oxaliplatin suffered neurotoxicity at a cumulative dose of 780 to 850 mg/m$^2$, while the risk increased to 50% at cumulative dose of 1170 mg/m$^{2[7]}$. The body of the experimental evidence suggests that dorsal root ganglion (DRG) neurons are the main target of platinum drug-induced CIPN[8, 9]. Oxaliplatin acts on the DRG, leading to the damage of the cell bodies[10, 11], alterations in nuclearus morphology[12], selective atrophy of subpopulation of neurons[13], and degeneration of peripheral nerve axons[14]. The severity of damage and degeneration of DRG depend on doses and schedule of oxaliplatin administration. Pathologic changes in peripheral nerves are slighter than that of DRG. The phenomenon of axonal degeneration can only be seen for a few times, and the structure of myelin is basically normal. It has been reported that oxaliplatin can significantly reduce the volume of nucleolus of DRG neuron in mouse, and slow down the nerve conduction velocity[15]. The mechanism underlying oxaliplatin-induced chronic neurotoxicity is that oxaliplatin inhibits the synthesis of rRNA and protein in the nucleolus of neuronal cell bodies, resulting in morphological change and damage of sensory neurons[16].

Since CIPN seriously affects the efficacy of chemotherapy, the researchers throughout the world are actively looking for effective drugs and methods for treating and preventing oxaliplatin-indued peripheral neurotoxicity. Based on the mechanism of oxaliplatin-induced neurotoxicity, a series of methods have been proposed for CIPN control, but the results are unsatisfactory. Carbamazepine, a Na$^+$ channel blocker, has been used in clinical studies for preventing the neurotoxicity of oxaliplatin. However, its preventive activity is shadowed in doubt because of its significant individual differences in plasma concentrations and adverse reactions including dizziness, somnolence, ataxia and others[17]. Amifostine, a preventive protector for the nephrotoxicity of cisplatin, is effective for treating oxaliplatin-induced peripheral neuropathy, but its cost is higher than the cost of chemotherapy per se. Clinical studies also indicated that gabapentin, calcium/magnesium salts, GSH, N-acetylcysteine and other drugs are effective for oxaliplatin-induced neurotoxicity, but their efficacy needs to be confirmed in the large-scale, randomized, and double-controlled experiments[18-20].

Oxaliplatin-induced neuropathy has a great impact on the quality of life of cancer patients. There are no curative conventional treatments, so further options have to be investigated. Traditional Chinese medicine (TCM) is a system of healing that is thousands of years old. It has long been proven successful treatment for chronic diseases and has also played an important role in the provision of health care in China. Based on clinical manifestation, CIPN belongs to the category of "arthralgia" in Chinese medicine. Its etiology and pathogenesis can be viewed in traditional Chinese medicine as qi and blood stagnation, damp accumulation, or kidney yin/yang deficiency. According to the principle in traditional Chinese medicine, i.e. the diagnosis and treatment should be made based on an overall analysis of the illness and the patient's condition, reinforcing Qi and nourishing Yin, as well as promoting blood circulation and removing obstruction in vessels, are major treatment methods for CIPN. Hence, taking the advantages of traditional Chinese medicine fully, there is a great potential to develop medicines that are effective, safe and cheap for preventing and treating CIPN from natural medicine resource, providing an adjuvant or alternative treatment to conventional treatment.

REFERENCES

[1] Jemal A, Bray F, Center M M, Ferlay J, Ward E, et al. Global Cancer Statistics. Cancer J Clin. 2011, 61: 69-90.

[2] Park S B, Goldstein D, Krishnan A V, Lin C S, Friedlander M L, et al. Chemotherapy-induced peripheral neurotoxicity: A critical analysis. CA Cancer J Clin. 2013, doi: 10.1002/caac.21204.

[3] Lavoie Smith E M, Li L, Hutchinson R J, Ho R, Burnette W B, et al. Measuring vincristine-induced peripheral neuropathy in children with acute lymphoblastic leukemia. Cancer Nurs. 2013, 36: 49-60.

[4] Argyriou A A, Polychronopoulos P, Iconomou G, Chroni E, Kalofonos H P. A review on oxaliplatin-induced peripheral nerve damage. Cancer Treat Rev 2008, 34: 368-377.

[5] Scripture C D, Figg W D, Sparreboom A. Peripheral Neuropathy Induced by Paclitaxel: Recent Insights and Future Perspectives. Curr Neurophamacol. 2006, 4: 165-172.

[6] Leandro-Garcia L J, Leskelä S, Jara C, Gréen H, Avall-Lundqvist E, et al. Regulatory polymorphisms in β-tubulin IIa are associated with paclitaxel-induced peripheral neuropathy. Clin Cancer Res. 2012, 18: 4441-4448.

[7] Cersosimo R J. Oxaliplatin-associated neuropathy: a review. Ann Pharmacother. 2005, 39: 128-135.

[8] Joseph E K, Chen X, Bogen O, Levine J D. Oxaliplatin acts on IB4-positive nociceptors to induce an oxidative stress-dependent acute painful peripheral neuropathy. J Pain 2008, 9: 463-472.

[9] Scuteri A, Galimberti A, Ravasi M, Pasini S, Donzelli E, et al. NGF protects dorsal root ganglion neurons from

[10] Donzelli E, Carfi M, Miloso M, Strada A, Galbiati S, Bayssas M, Griffon-Etienne G, Cavaletti G, Petruccioli M G, Tredici G. Neurotoxicity of platinum compounds: Comparison of the effects of cisplatin and oxaliplatin on the human neuroblastoma cell line SH-SY5Y. J Neurooncol 2004, 67: 65-73

[11] Ta L E, Espeset L, Podratz J, Windebank A J. Neurotoxicity of oxaliplatin and cisplatin for dorsal root ganglion neurons correlates with platinum-DNA binding. Neurotoxicology, 2006, 27:992-1002.

[12] Cavaletti G, Tredici G, Petruccioli M G, Dondè E, Tredici P, Marmiroli P, Minoia C, Ronchi A, Bayssas M, Etienne G G. Effects of different schedules of oxaliplatin treatment on the peripheral nervous system of the rat. Eur J Cancer 2001, 37: 2457-2463.

[13] Jamieson S M, Liu J, Connor B, McKeage M J: Oxaliplatin causes selective atrophy of a subpopulation of dorsal root ganglion neurons without inducing cell loss. Cancer Chemother Pharmacol. 2005; 56: 391-399.

[14] Renn C L, Carozzi V A, Rhee P, Gallop D, Dorsey S G, Cavaletti G. Multimodal assessment of painful peripheral neuropathy induced by chronic oxaliplatin-based chemotherapy in mice. Mol Pain, 2011, 7:29.

[15] Renn C L, Carozzi V A, Rhee P, Gallop D, Dorsey S G, Cavaletti G. Multimodal assessment of painful peripheral neuropathy induced by chronic oxaliplatin-based chemotherapy in mice.

[16] Weickhardt A, Wells K, Messersmith W. Oxaliplatin-Induced Neuropathy in Colorectal Cancer. J Oncology, 2011, 2011: 201593.

[17] Hoffman K R. Potential prevention and treatment of oxaliplatin associated peripheral neuropathy. J Clin Oncol. 2004, 22: 8093.

[18] Cascinu S, Catalano V, Cordella L, Labianca R, Giordani P, et al. Neuroprotective Effect of Reduced Glutathione on Oxaliplatin-Based Chemotherapy in Advanced Colorectal Cancer: A Randomized, Double-Blind, Placebo-Controlled Trial. J Clin Oncol. 2002, 20: 3478-3483.

[19] Wen F, Zhou Y, Wang W, Hu Q C, Liu Y T. Ca/Mg infusions for the prevention of oxaliplatin-related neurotoxicity in patients with colorectal cancer: a meta-analysis. Ann Oncol. 2012, 00: 1-8.

[20] Grothey A, Nikcevich D A, Sloan J A, Kugler J W, Silberstein P T. Intravenous Calcium and Magnesium for Oxaliplatin-Induced Sensory Neurotoxicity in Adjuvant Colon Cancer: NCCTG N04C7. J Clin Oncol. 2011, 29: 421-427.

SUMMARY OF THE INVENTION

The technical problem to be solved by the present invention is to provide a pharmaceutical composition for treating cancer, which can significantly reduce peripheral neuropathic side effects induced by chemotherapeutic drugs.

In order to solve the above technical problem, the technical solution adopted by the present invention is as follows:

A pharmaceutical composition for treating cancer, comprising:

(1) a herbal composition generated from *Astragali membranaceus* radix, *Cinnamomi cortex*, *Paeonia alba* radix, *Jujubae fructus*, and *Zingiberis rhizoma* or an extract of the above mixed herbal medicine;

(2) one or more chemotherapeutic compounds.

Wherein the pharmaceutical composition for treating cancer of the present invention can also comprise pharmaceutically acceptable carriers.

Wherein said chemotherapeutic compound is a chemotherapeutic agent for cancer. Said chemotherapeutic agent for cancer includes, but is not limited to, oxaliplatin, cisplatin, carboplatin, taxol, vincristine, vinblastine and any one or more derivatives of all the above chemotherapeutic substances.

Wherein said herbal composition generated from *Astragali membranaceus* radix, *Cinnamomi cortex*, *Paeonia alba* radix, *Jujubae fructus*, and *Zingiberis rhizoma* is preferably selected from a mixture of *Astragali membranaceus* radix, *Cinnamomi cortex*, *Paeonia alba* radix, *Jujubae fructus*, and *Zingiberis rhizoma* at the ratio by weight of 2~4:1~3:1~3: 1~3:1~3, most preferably selected from a mixture of *Astragali membranaceus* radix, *Cinnamomi cortex*, *Paeonia alba* radix, *Jujubae fructus*, and *Zingiberis rhizoma* at the ratio by weight of 2:1:1:1:1.

Wherein said extract of mixed herbal medicine can be prepared according to the following process: five single-herb herbal medicines *Astragali membranaceus* radix, *Cinnamomi cortex*, *Paeonia alba* radix, *Jujubae fructus*, and *Zingiberis rhizoma* are mixed at a specific ratio by weight, water is added and heated to reflux for 1~3 hours., The extraction is performed 1~3 times. The liquid extracts are combined after filtration. Wherein the ratio by weight of *Astragali membranaceus* radix, *Cinnamomi cortex*, *Paeonia alba* radix, *Jujubae fructus*, and *Zingiberis rhizoma* is preferably 2~4: 1~3:1~3:1~3:1~3. In the most preferred embodiment, the weight ratio of *Astragali membranaceus* radix, *Cinnamomi cortex*, *Paeonia alba* radix, *Jujubae fructus*, and *Zingiberis rhizoma* is 2:1:1:1:1. The extract of mixed herbal medicine of the present invention can be in the form of liquid extract, or the liquid extract can be prepared into concentrated extract or soft material. All the above processes are well known to those skilled in the art.

Use of a pharmaceutical composition in the preparation of medicament for treating human cancer, wherein said pharmaceutical composition comprises:

(1) a herbal composition generated from *Astragali membranaceus* radix, *Cinnamomi cortex*, *Paeonia alba* radix, *Jujubae fructus*, and *Zingiberis rhizoma* or an extract of the above mixed herbal medicine;

(2) one or more chemotherapeutic compounds.

Wherein the pharmaceutical composition for treating cancer of the present invention can further comprise pharmaceutically acceptable carriers.

Wherein said herbal composition generated from *Astragali membranaceus* radix, *Cinnamomi cortex*, *Paeonia alba* radix, *Jujubae fructus*, and *Zingiberis rhizoma* is preferably selected from a mixture of *Astragali membranaceus* radix, *Cinnamomi cortex*, *Paeonia alba* radix, *Jujubae fructus*, and *Zingiberis rhizoma* at the ratio by weight of 2~4:1~3:1~3: 1~3:1~3, most preferably selected from a mixture of *Astragali membranaceus* radix, *Cinnamomi cortex*, *Paeonia alba* radix, *Jujubae fructus*, and *Zingiberis rhizoma* at the ratio by weight of 2:1:1:1:1.

Wherein said extract of mixed herbal medicine can be prepared according to the following process: *Astragali membranaceus* radix, *Cinnamomi cortex*, *Paeonia alba* radix, *Jujubae fructus*, and *Zingiberis rhizoma* are mixed at a specific ratio by weight, water Water is added and heated to reflux for 1~3 hours. The extraction is performed 1~3 times. The liquid extracts are combined after filtration. Wherein the ratio by weight of *Astragali membranaceus* radix, *Cinnamomi cortex*, *Paeonia alba* radix, *Jujubae fructus*, and *Zingiberis rhizoma* is preferably 2~4:1~3:1~3:1~3:1~3, most preferably 2:1:1:1:1. The extract of mixed herbal medicine of the present invention can be in the form of liquid extract, or the liquid extract can be prepared into concentrated extract or soft material. All the above processes are well known to those skilled in the art.

Wherein said chemotherapeutic compound is a chemotherapeutic agent for cancer. Said chemotherapeutic agent for cancer includes, but is not limited to, cisplatin, carboplatin, oxaliplatin, taxol, vincristine, vinblastine and any one or more derivatives of all the above chemotherapeutic substances.

Wherein said cancer is stomach cancer, colon cancer, breast cancer, ovarian cancer and the like.

Use of a pharmaceutical composition in the preparation of medicament for reducing side effects of chemotherapeutic compound in human body, wherein said pharmaceutical composition comprises:
(1) a herbal composition generated from *Astragali membranaceus* radix, *Cinnamomi cortex, Paeonia alba* radix, *Jujubae fructus*, and *Zingiberis rhizoma* or an extract of the above mixed herbal medicine;
(2) one or more chemotherapeutic compounds.

Wherein the pharmaceutical composition for treating cancer of the present invention can further comprise pharmaceutically acceptable carriers.

Wherein said herbal composition generated from *Astragali membranaceus* radix, *Cinnamomi cortex, Paeonia alba* radix, *Jujubae fructus*, and *Zingiberis rhizoma* is preferably selected from a mixture of *Astragali membranaceus* radix, *Cinnamomi cortex, Paeonia alba* radix, *Jujubae fructus*, and *Zingiberis rhizoma* at the ratio by weight of 2~4:1~3:1~3:1~3:1~3, most preferably selected from a mixture of *Astragali membranaceus* radix, *Cinnamomi cortex, Paeonia alba* radix, *Jujubae fructus*, and *Zingiberis rhizoma* at the ratio by weight of 2:1:1:1:1.

Wherein said extract of mixed herbal medicine can be prepared according to the following process: *Astragali membranaceus* radix, *Cinnamomi cortex, Paeonia alba* radix, *Jujubae fructus*, and *Zingiberis rhizoma* are mixed at a specific ratio by weight, water is added and heated to reflux for 1~3 hours. The extraction is performed 1~3 times. The liquid extracts are combined after filtration. Wherein the ratio by weight of *Astragali membranaceus* radix, *Cinnamomi cortex, Paeonia alba* radix, *Jujubae fructus*, and *Zingiberis rhizoma* is preferably 2~4:1~3:1~3:1~3:1~3, most preferably 2:1:1:1:1. The extract of mixed herbal medicine of the present invention can be in the form of liquid extract, or the liquid extract can be prepared into concentrated extract or soft material. All the above processes are well known to those skilled in the art.

Wherein said chemotherapeutic compound is a chemotherapeutic agent for cancer. Said chemotherapeutic agent for cancer includes, but is not limited to, oxaliplatin, cisplatin, carboplatin, taxol, vincristine, vinblastine and any one or more derivatives of all the above chemotherapeutic substances.

Wherein said side effect is peripheral neuropathy induced by chemotherapeutic compound, including one or more of the following symptoms: acroanesthesia, pain, glove- or sock-like feeling, cold skin, paresthesia, formication, powerlessness, feeling like walking on cotton, burning-like pain, shooting pain, cutting-like pain and the like.

Use of a pharmaceutical composition in the preparation of medicament for reducing side effects of chemotherapeutic compound in human body, wherein said pharmaceutical composition is a herbal composition generated from *Astragali membranaceus* radix, *Cinnamomi cortex, Paeonia alba* radix, *Jujubae fructus*, and *Zingiberis rhizoma* or an extract of the above mixed herbal medicine.

Wherein said chemotherapeutic compound is a chemotherapeutic agent for cancer. Said chemotherapeutic agent for cancer includes, but is not limited to, oxaliplatin, cisplatin, carboplatin, taxol, vincristine, vinblastine and any one or more derivatives of all the above chemotherapeutic substances.

Wherein said side effect is peripheral neuropathy induced by chemotherapeutic compound, including one or more of the following symptoms: acroanesthesia, pain, glove- or sock-like feeling, cold skin, paresthesia, formication, powerlessness, feeling like walking on cotton, burning-like pain, shooting pain, cutting-like pain and the like.

The pharmaceutical composition of the present invention is generally administered in the way of drug combination, i.e. the herbal composition generated from *Astragali membranaceus* radix, *Cinnamomi cortex, Paeonia alba* radix, *Jujubae fructus*, and *Zingiberis rhizoma* or the extract of the above mixed herbal medicine is administered in combination with one or more chemotherapeutic compounds.

Colorectal cancer is one of the most common malignant tumors in human, and it ranks third in incidence among the malignant tumors in the world. In China, the incidence of colorectal cancer is found to be gradually increased, ranking fifth in death caused by malignant tumors. The drug combination of oxaliplatin/5-FU/LV is the first-line therapy for treating advanced colorectal cancer in patients[21]. Oxaliplatin is a diaminocyclohexane-platinum compound, which can form platinum-DNA adduct in cell, and destroy the integrity of DNA. However, for patients receiving chemotherapy, the identified peripheral neuropathy is one of the dose-limiting toxicities of oxaliplatin, cisplatin, taxol and other chemotherapeutic drugs.

The results of animal pharmacodynamic experiments and clinical studies in the present invention indicated that the herbal composition generated from *Astragali membranaceus* radix, *Cinnamomi cortex, Paeonia alba* radix, *Jujubae fructus*, and *Zingiberis rhizoma* or the extract of the above mixed herbal medicine (AC591 for short hereinafter) can markedly reduce the toxicity induced by chemotherapeutic drugs, prevent the occurrence of peripheral neuropathy, and enhance the antitumor effect of oxaliplatin.

Advantageous Effects: the pharmaceutical composition of the present invention can reduce peripheral neuropathic side effects induced by chemotherapeutic drugs, increase tolerance dosages of anticancer drugs, and enhance efficacy of anticancer drugs. During the chemotherapy treatment, the patients who administer the composition of the present invention exhibit good compliance without adverse reactions. The pharmaceutical composition of the present application is safe and suitable for clinical practice.

REFERENCE

[21] Andre T, Boni C, Mounedji-Boudiaf L, et al. Oxaliplatin, fluorouracil, and leucovorin as adjuvant treatment for colon cancer. N. Engl. J. Med. 2004, 350: 2343-2351.

DETAILED DESCRIPTION OF THE EMBODIMENTS

Figure 1:
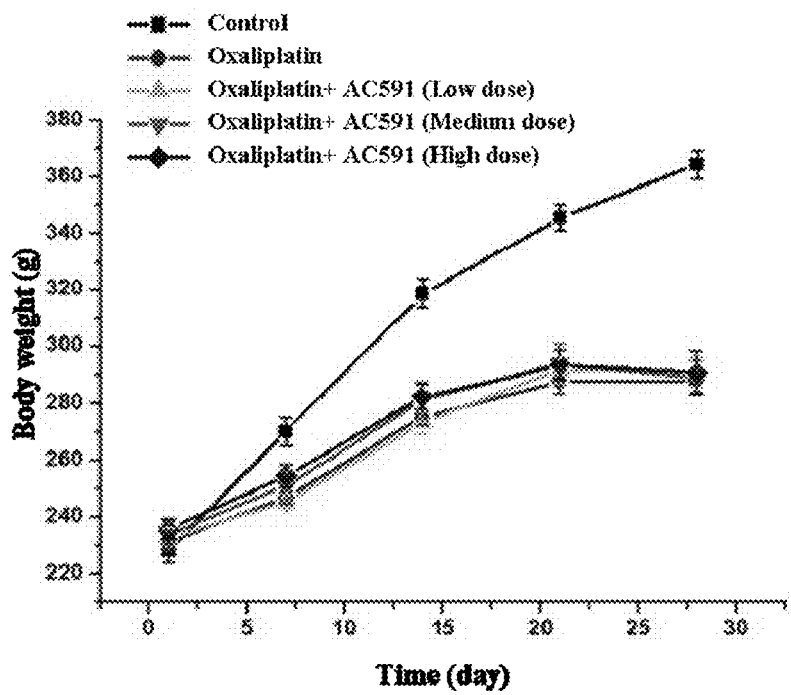
FIG. 1. The effects of herbal composition AC591 on body weights of CIPN rats

According to the following examples, the present invention can be better understood. However, those skilled in the art would readily appreciate that the content described in the examples is merely used to explain the present invention, which should not and would not limit the scope of the present invention as described in details in claims.

Example 1

Study on the Protective Effect of Herbal Composition AC591 on Oxaliplatin-Induced Peripheral Neuropathy in Rats 1. Experimental Materials Experimental Drugs: Oxaliplatin lyophilized powder (AiHeng) (50 mg, batch number: 1103211) was purchased from Jiangsu Hengrui Medicine Co., Ltd.

Instruments: Von frey hairs test for pain sensation (Stoelting Company, USA), Leica RM2135 rotary tissue slicer (Germany), ABI7500 fluorescence quantitative PCR instrument (ABI, USA).

Experimental Animals: Male Waistar rats weighting 180-200 g were purchased from Shanghai Slac Laboratory Animal Center and used for the oxaliplatin-induced peripheral neuropathy model. Animals were housed 3 per cage in a temperature- and humidity-controlled environment under a 12/12-h light/dark cycle. Food and water were freely available. All experimental procedures were approved by the Animal Experimental committee of Jiangsu Province Academy of Traditional Chinese Medicine. All efforts were made to minimize the number of animals used and their suffering.

Preparation of Oxaliplatin Solution: Oxaliplatin lyophilized powder was dissolved in 5% glucose solution (5 g/100 ml), with final concentration of 1 mg/ml.

Preparation of Herbal Extract: The extract of herbal composition AC591 was prepared as follows: *Astragali membranaceus* radix, *Cinnamomi cortex*, *Paeonia alba* radix, *Jujubae fructus*, and *Zingiberis rhizoma* were mixed. Ten times amount of water (v/w) was added, and heated to reflux for 2 hours. The extraction was performed 2 times. After filtration, the liquid extracts were combined and concentrated under vacuum into a thick paste. Wherein the ratio by weight of *Astragali membranaceus* radix, *Cinnamomi cortex*, *Paeonia alba* radix, *Jujubae fructus*, and *Zingiberis rhizoma* was preferably 2:1:1:1:1. The herbal composition extract was stored at −20° C. and used within 30 days. Before each gavage, the thick paste was diluted with a certain volume of saline to the desired concentration, and then incubated in water at 80° C. for 30 minutes. During the storage period, residual precipitate appeared in the solution. Therefore, the solution needed to be suspended via a vortex mixer prior to administration to animals.

2. Experimental Methods (1) Animal Grouping: the rats were randomly divided into five groups by using randomized grouping method (N=10 rats/group):

Group 1: saline (control group)
Group 2: oxaliplatin+saline (model group)
Group 3: oxaliplatin+AC591 (20 g crude drug/kg) (high dose)
Group 4: oxaliplatin+AC591 (10 g crude drug/kg) (medium dose)
Group 5: oxaliplatin+AC591 (5 g crude drug/kg) (low dose)

(2) Modeling and Administration: The first day of drug treatment was referred to as d1. In Group 1, oxaliplatin (4 mg/kg) was administered intraperitoneally twice per week for 4 weeks (d1, d2, d8, d9, d15, d16, d22, d23). In groups 3, 4 and 5, in addition to oxaliplatin (4 mg/kg), AC591 extracts was administered orally once daily for 4 weeks. In group 2, 0.9% NaCl solution was administered orally once daily for 4 weeks in addition to oxaliplatin administration (1 ml for each time).

(3) Measurement of Index: The rats were weighed every 5 days, and behavioral tests were conducted before oxaliplatin administration at specific times on all experimental animals. After the last administration, the rats were sacrificed. Spinal cord and L5 dorsal root ganglia were harvested from all experimental animals, and taken to make tissue sections, which were stained with Nissl staining to observe the extent of damage in neurons. The expressions of pain-related TRP ion channel proteins, TRPMS, TRPV1, and TRPA1 mRNA, in dorsal root ganglion tissue were determined by qPCR assay.

(4) Von Frey test for mechanical allodynia: According to the method described by Chaplan et al[22], the mechanical allodynia was assessed by von Frey test. Rats were placed in a clear plastic box (22×12×22 cm) with a wire mesh floor and allowed to habituate for 15 min prior to testing. Von Frey filaments ranging 1-15 g bending force were applied to the midplantar skin of each hind paw with each application held for 4 s. Withdrawal responses to the stimulation of von Frey filaments were recorded and paw withdrawal thresholds were determined by a modified up-down method. Each von Frey filament with equivalent force was measured for five times, and the time interval between simulations was 30 seconds, 3 or more times of positive reactions out of 5 simulations was deemed to be mechanical allodynia.

3. Experimental Results (1) Effect of Herbal Composition AC591 on the Body Weight of CIPN Rats As shown in FIG. 1, the body weight of rat in control group presented a rising trend over time. Due to oxaliplatin administration, rats in model group were subjected gastrointestinal adverse reactions, with slower weight gain or even weight loss. After 7 days of modeling, the body weight of rats in model group was significantly lower than that of rats in control group, and there was statistical significance therebetween. However, herbal composition AC591 had no obvious effect on the improvement with respect to oxaliplatin-induced weight loss in rats.

(2) Effect of Herbal Composition AC591 on Mechanical Allodynia in CIPN Rats

Figure 2:
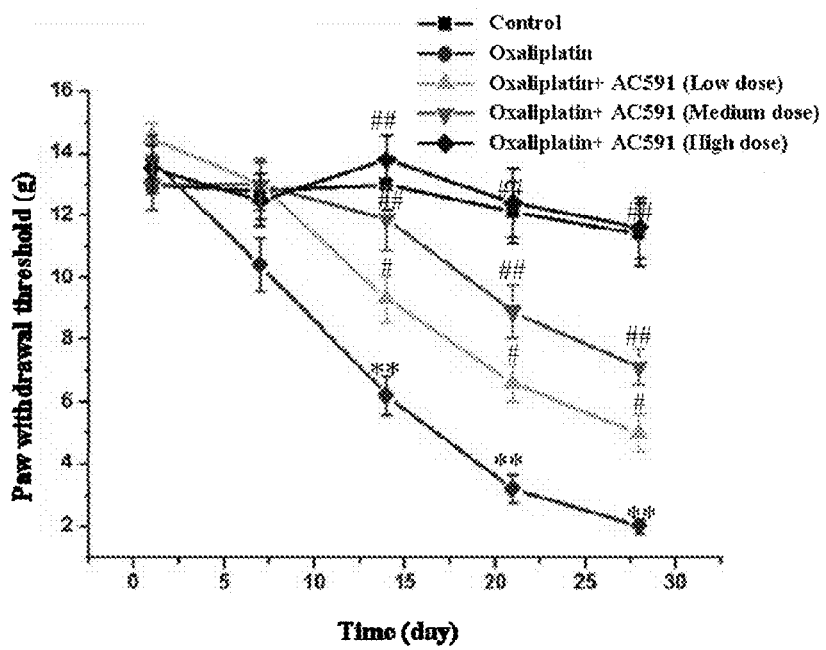
FIG. 2. The effects of herbal composition AC591 on mechanical allodynia of CIPN rats in von Frey test (compared with normal group, *$P<0.05$, **$P<0.01$; compared with model group, #$P<0.05$, ##$P<0.01$)

Mechanical paw-withdrawing threshold in rats in control group tended to be stabilized. 14 days after the experiment, the rat in model group showed significant allodynia. The mechanical paw-withdrawing threshold thereof was significantly decreased as compared with that of control group (P<0.05). The repeated administration of AC591 had a strong effect on attenuation of oxaliplatin-induced reduction of withdrawal threshold. As compared with model group, the withdrawal threshold in rats in low-, medium- and high-dose AC591 groups were significantly increased (P<0.05 or P<0.01) with a dose effect relationship. Wherein there was no significant difference in withdrawal threshold of rats between high-dose AC591 and control groups, indicating that a high dose of herbal composition AC591 could prevent peripheral neuropathy induced by oxaliplatin. The results were seen in FIG. 2.

(3) Protective Effect of Herbal Composition AC591 on DRG Neutrons of CIPN Rats

Figure 3:
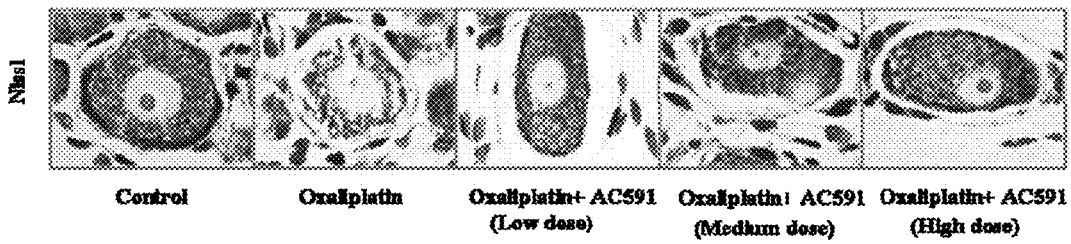
FIG. 3. The effects of herbal composition AC591 on DRG neutrons of CIPN rats

As shown in FIG. 3, the DRG neurons of rats in control group were located at the periphery of DRG, with larger nuclei and nucleoli. However, for rats in model group, part of cell bodies and nuclei of neurons greatly shrinked, outline of nuclear membrane appeared vague or even disappeared, and the nucleolus was obviously pyknotic. The high-, medium- and low-dose of AC591 extract could significantly improve neuronal damage caused by oxaliplatin, and make neuronal nuclei and nucleoli become normal, showing a protective effect on the sensory nerves.

Figure 4:
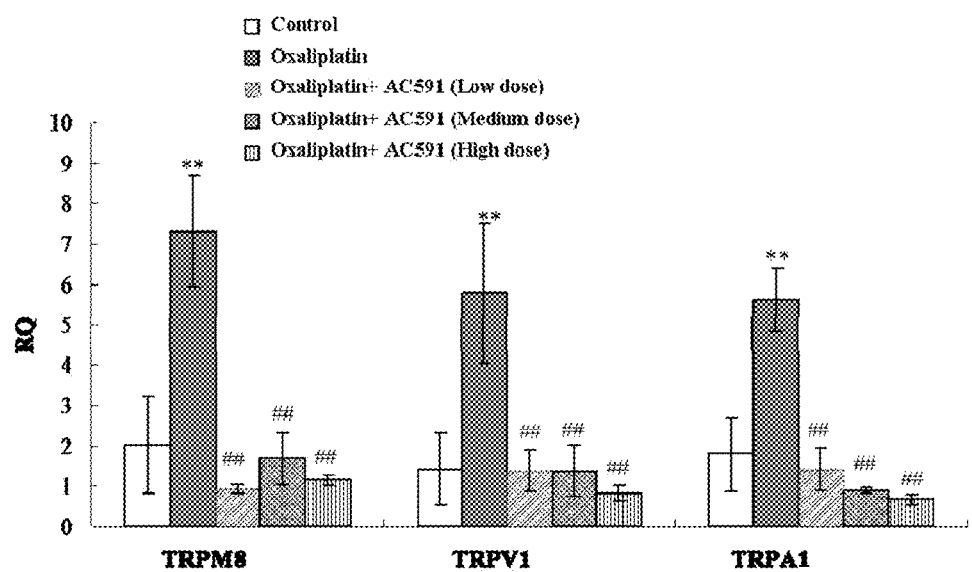
FIG. 4. The effects of herbal composition AC591 on the expression of pain-related transient receptors potential ion channel protein (compared with normal group, *P<0.05, **P<0.01; compared with model group, #P<0.05, ##P<0.01)

(4) Effect of Herbal Composition AC591 on the Expression of Pain-Related TRP Ion Channel Proteins To elucidate the mechanism of the preventive effect of AC591 on oxaliplatin-induced peripheral neuropathy, we determined the expression of TRPM8, TRPV1 and TRPA1 mRNA in L4-L6 DRG using real-time PCR. As shown in FIG. 4, the expression of TRPM8, TRPV1 and TRPA1 mRNA in model group was significantly increased 2-4 fold as compared with the expression in the control group (P<0.01). In contrast, the expressions of mRNA in rats treated with herbal composition AC591 were greatly decreased (P<0.01, compared with model group). The mRNA expression levels of TRPA1 and TRPV1 in herbal composition AC591 groups were almost identical to those in the control group. These results suggested that oxaliplatin-induced peripheral neuropathy is involved in overexpression of TRPM8, TRPV1 and TRPA1 mRNA. And the protective effect of AC591 is involved in the expression of TRPM8, TRPV1 and TRPA1 mRNA increased by oxaliplatin administration.

4. Conclusion

In this experiment, behavioral test and histological analysis showed that chemotherapy-induced peripheral neuropathy model was prepared successfully. AC591 ameliorated oxaliplatin-induced mechanical allodynia and DRG neuron damage. The AC591 improved the oxaliplatin-induced peripheral neuropathy by suppressing the overexpression of TRPM8, TRPV1 and TRPA1 channels. These findings indicated that AC591 is a medicine useful for reducing the adverse effects of oxaliplatin administration, and thus to improve the quality of life of patients treated with oxaliplatin.

REFERENCES

[22] Chaplan S R, Bach F W, Pogrel J W, et al., Quantitative assessment of tactile allodynia in the rat paw. *J Neurosci. Methods*, 1994, 53: 55-63.

Example 2

The Effect of Herbal Composition AC591 on Anti-Tumor Activity of Oxaliplatin

1. Experimental Materials

Experimental Drugs: Oxaliplatin lyophilized powder (AiHeng, batch number: 1103211) was purchased from Jiangsu Hengrui Medicine Co., Ltd.; 100 ml of 5% glucose injection (5 g, batch number 2012051801), 100 ml of sodium chloride injection (0.9 g, batch number 12012091203), and TCM were purchased from the pharmacy of Jiangsu Provincial Hospital of Integrated Traditional Chinese and Western Medicine.

Instruments: Desktop ordinary centrifuge, desktop frozen centrifuge, cryogenic refrigerators and carbon dioxide incubator were from Eppendorf Company. Inverted microscope is purchased from Olympus Company.

Experimental Animals and Cell Lines: Six-week-old Balb/c mice weighing (16±2) g, bisexual each half, were purchased from Shanghai Slac Laboratory Animal Center and kept in SPF Laboratory Animal Room in Institute of Chinese Medicine and Pharmacy of Jiangsu Province. CT26 murine colorectal cancer cells were obtained from molecular biology laboratory of Institute of Chinese Medicine and Pharmacy of Jiangsu Province.

Preparation of Oxaliplatin Solution: Oxaliplatin lyophilized powder was dissolved in 5% glucose solution (5 g/100 ml). The final concentration of oxaliplatin was prepared as 1 mg/ml.

Preparation of Herbal Extract: The herbal composition AC591 extract was prepared as described in Example 1.

2. Experimental Methods (1) Modeling of Colorectal Cancer Subcutaneous Xenograft CT26 cells were cultured in Dulbecco's Modified Eagle Medium with 2.0 g/l sodium bicarbonate plus 10% fetal bovine serum, 1% L-glutamine, 100 U/ml penicillin and 100 U/ml streptomycin. When the cells were approximately 80% confluent, the culture medium was discarded and washed with PBS. Trypsin was then introduced to perform digestion. When the connection between cells appeared loose, the trypsin was discarded, and cell culture medium was introduced to terminate the digestion. Cells were repeatedly and gently pipetted with a pipette so as to be taken off the wall to form cell suspension. It was collected into centrifuge tubes and centrifuged. The concentration of cell suspension was adjusted to $1 \times 10^6/0.2$ ml with 0.9% sterile saline. A suspension of C-26 cells (0.2 ml each) were inoculated s.c. into the left flanks of BALB/c mice.

(2) Grouping and Administration

Eight days later when the tumor volume reached 100 mm$^3$, the mice were randomly divided into five groups in a manner to equalize the mean tumor among the five groups (N=8 each).

Group 1: saline (control group)
Group 2: oxaliplatin+saline (oxaliplatin group)
Group 3: oxaliplatin+AC591 (4 g crude drug/ml) (high dose)
Group 4: oxaliplatin+AC591 (2 g crude drug/ml) (medium dose)
Group 5: oxaliplatin+AC591 (1 g crude drug/ml) (low dose)

Group 1 and group 2 respectively received 0.1 ml 0.9% normal saline and 5 mg/kg oxaliplatin (i.p.) plus saline solution. For groups 3, 4 and 5, in addition to oxaliplatin (5 mg/kg), high-, medium- and low-dose AC591 extract was given as gavage to mice daily for 2 weeks, and the injection volume was 0.2 ml. Tumor volume and body weight were recorded every 3 days, and the tumor volume was calculated using the formula: tumor volume (mm$^3$)=length (mm)×width (mm)$^2$/2. After 2 weeks treatment, all mice were sacrificed and then tumor was segregated and weighed.

3. Experimental Results

Figure 5:
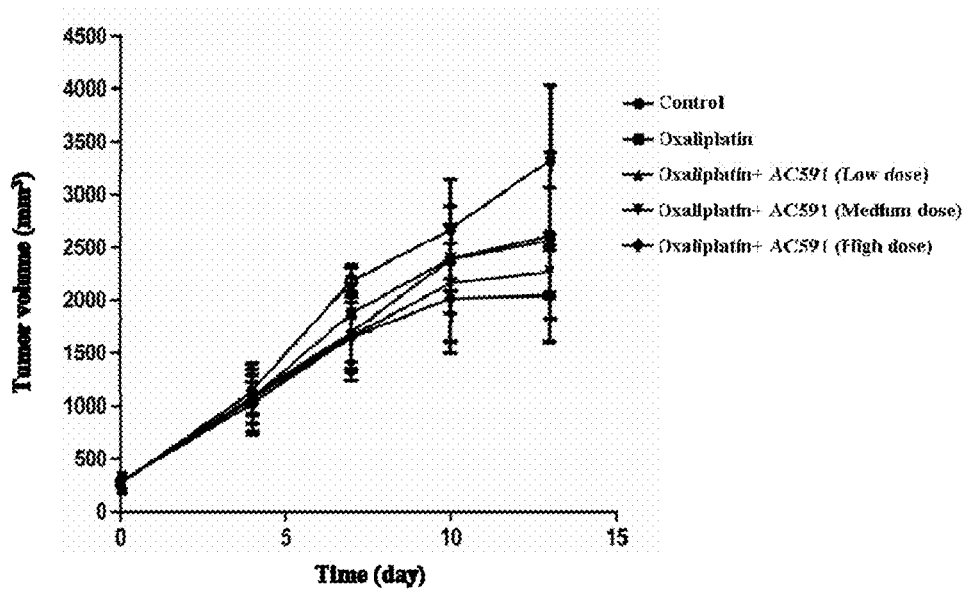
FIG. 5. The effects of herbal composition AC591 on anti-tumor activity of oxaliplatin FIG. 6. The effects of herbal composition AC591 on body weights of tumor cells-implanted mice FIG. 7. The number of cases in the occurrence of neurotoxicity in patients after the fourth treatment cycles FIG. 8. The clinical efficacy of AC591 against chemotherapy-induced periphery neurotoxicity
Figure 6:
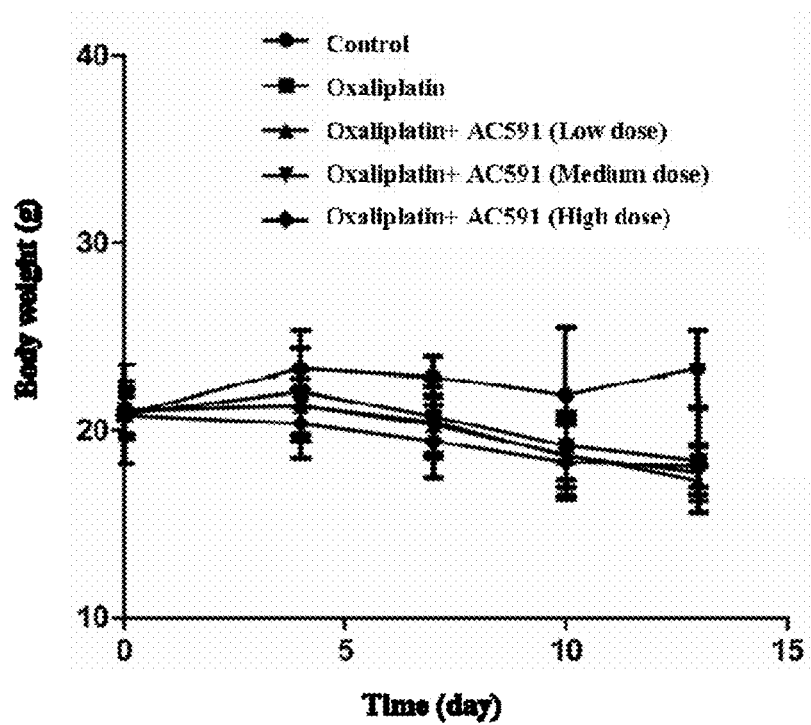

As shown in FIG. 5, oxaliplatin (5 mg/kg, i.p.) significantly inhibited the increase of tumour volumes compared with vehicle on days 4 and 7 in tumour cells-implanted mice (P<0.05 by Student's t-test). The combination administration of oxaliplatin and AC591 extract showed a better anti-tumor effect than oxaliplatin administered alone. High-dose of AC591 extract could significantly enhance the anti-tumor activity of oxaliplatin in Balb/c mice carrying CT26 tumors (P<0.05). However, the result shown in FIG. 6 showed that there were no significant difference in the change of body weight between oxaliplatin administered alone and oxaliplatin administered in combination with AC591 extract.

Example 3

Clinical Observation of Herbal Composition AC591 on the Treatment of Oxaliplatin-Induced Peripheral Neurotoxicity 1. Eligibility Criteria A total of 48 eligible patients with an average age of 52.5 years were enrolled in the study. Of these, 32 cases were colon cancers, and 16 cases were colorectal cancer. The patients were randomly divided into AC591-treated group and placebo group. There were no significant differences in gender, age, condition and the like between two groups (P>0.05). Inclusion Criteria: there is a clear cytological or pathological proof for diagnosing colorectal cancer in patient; both are suitable to apply the oxaliplatin-containing regimen to perform chemotherapy; Kamofsky score >60 points; routine blood test, liver and kidney function, and heart and lung function are normal; expected period of survival >3 months; informed consent is available; good compliance, obedient to the arrangements of physician, free access to medical follow-up. Exclusion criteria: patient with existing neurological diseases; patient with diabetes which may cause peripheral sensory abnormalities; oxaliplatin, vinca alkaloids, cisplatin, taxol and other drugs which can induce neurotoxicity and interfere with chemotherapy for patient have been or are being administered.

2. Treatment Plan

Patients in two groups were scheduled to receive 3 months (4 cycles) of adjuvant FOLFOX chemotherapy containing oxaliplatin. Briefly, the patients were treated with the protocol following: 130 mg/m$^2$ of oxaliplatin by intravenous infusion for 2-3 hours on day 1; 200 mg of calcium folinate by intravenous infusion for no less than half an hour on day 1-day 5; 0.5 g/m$^2$ of fluorouracil by intravenous infusion for 4-6 hours on day 1-day 5. This regimen was performed once for every 3 weeks.

Chemotherapy control group: patients were treated with FOLFOX chemotherapy regimen alone.

AC591-treated group: while the chemotherapy was given, an aqueous decoction of herbal composition AC591 was additionally administered. The aqueous decoction of AC591 was privately prepared by Jiangsu Province Hospital of Integrated Traditional Chinese and Western Medicine (preparation method: *Astragali membranaceus* radix, *Cinnamomi cortex*, *Paeonia alba* radix, *Jujubae fructus*, and *Zingiberis rhizoma* were mixed. Ten times amount of water (v/w) was added and heated to reflux for 2 hours. The extraction was performed 2 times. After filtration, the liquid extracts were combined and concentrated under vacuum into a thick paste.) and packed (100 ml/package). One package was administered every time, twice a day, till the end of chemotherapy. After completing four cycles of chemotherapy (21 days/cycle), clinical assessments to measure symptoms of neuropathy were carried out.

3. Observation Index and Evaluation Criteria (1) The overall incidence of neurotoxicity and the number of cases of peripheral nerve toxicity with various degrees (level 0-4) occurred in both groups of patients after four cycles of chemotherapy were evaluated by Levi's grading criteria: level 0, normal; level 1, paresthesia or dysesthesia (induced by cold) which can be completely dissipated within a week; level 2, paresthesia or dysesthesia which can be completely dissipated within 3 weeks; level 3, paresthesia or dysesthesia which cannot be completely dissipated within 3 weeks; level 4, paresthesia or dysesthesia accompanied by dysfunction.

(2) Study of clinical efficacy of AC591 against chemotherapy-induced periphery neurotoxicity.

Efficacy of AC591 was evaluated with Nimodipine trichotomy, namely (Value pre-treatment−Value post-treatment). According to grading standards, signs and symptoms between pre- and post-treatment were analyzed and compared.

Markedly effective: the effect of post-treatment is two or more levels lower than that of pre-treatment;

Effective: the effect of post-treatment is one level lower than that of pre-treatment Ineffective: peripheral neurotoxicity does not mitigate or aggravate Total efficacy rate (%)=(number of markedly effective cases+number of effective cases)/total number of cases×100%

Figure 7:
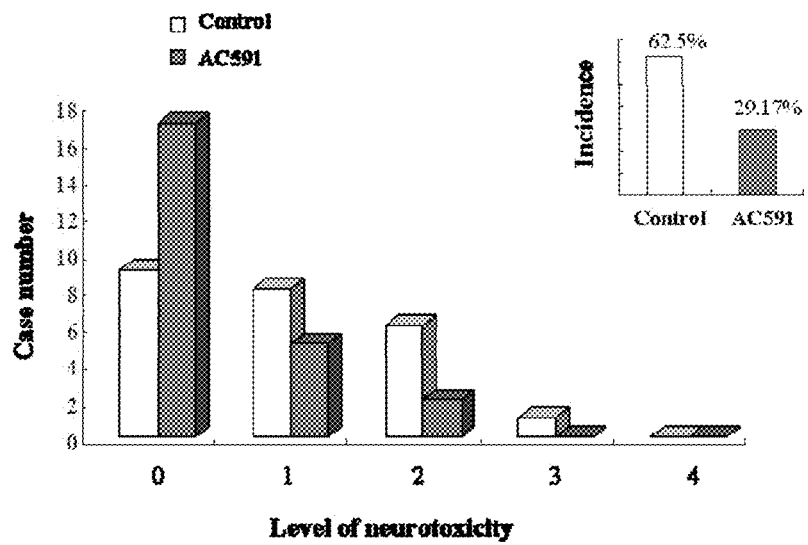

4. Results (1) The Total Incidence and Severity of Neurotoxicity after Four Cycles of Treatment In chemotherapy control group, the overall incidence of neurotoxicity was 62.5%, wherein the neurotoxicity at level 1-2 covered 14 cases, accounting for 93.75%, the neurotoxicity at level 3-4 covered one case, accounting for 6.25%. In the treatment group of herbal compositions AC591, the overall incidence of neurotoxicity was 29.17%, wherein the neurotoxicity at level 1-2 covered 7 cases, accounting for 100% (FIG. 7). There was a statistically significant difference in the incidence of peripheral neurotoxicity between the treatment group of herbal compositions AC591 and the control group of chemotherapy, suggesting that the composition of the present invention can alleviate oxaliplatin-induced peripheral neurotoxicity, especially chronic cumulative neurotoxicity.

(2) Evaluation of Efficacy

Figure 8:
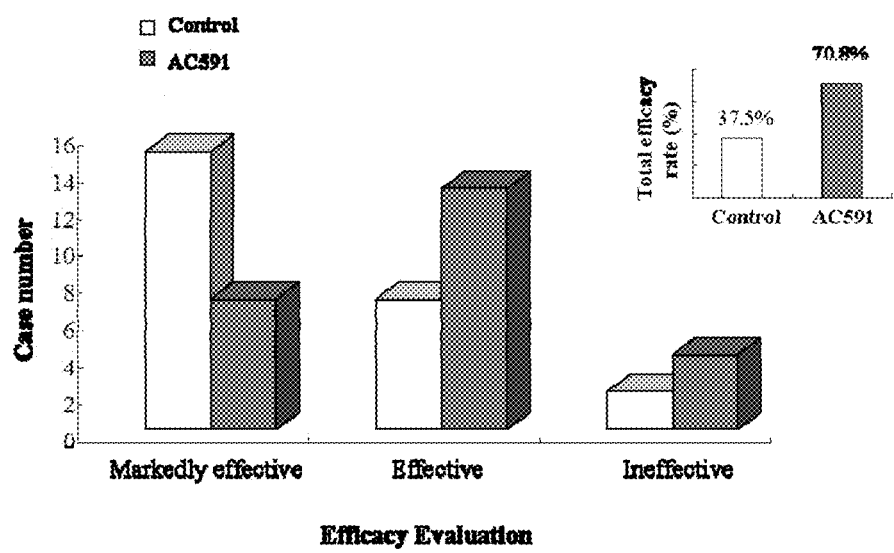

As shown in FIG. 8, the total effective rate of treatment group with herbal composition AC591 was 70.8% after four cycles treatment. Among the 24 cases, 4 cases markedly improved, 13 cases effected and 7 cases invalided. While in chemotherapy control group, 2 cases showed a marked effect, 7 got effect, 15 got failure, and the total effective rate was 37.5%. These results suggest that AC591 is effective in reducing the incidence and severity of peripheral neuropathy of cancer patients receiving oxaliplatin.

5. Conclusion

In the chemotherapy, the incidence of oxaliplatin-induced peripheral neurotoxicity is high, to a large extent, limiting its clinical application in the treatment of cancer. The composition of the present invention showed a preventive effect on oxaliplatin-induced peripheral neurotoxicity, delayed the occurrence of chronic cumulative neurotoxicity, and reduced the degree of neurotoxicity. During the chemotherapy, patients administered with the compositions of the present invention had a good compliance without any adverse reaction. Herbal composition AC591 is safe and suitable for clinical practice.

What is claimed is:

1. A composition consisting essentially of *Astragali membranaceus* radix extract, *Cinnamomi cortex* extract, *Paeonia alba* radix extract, *Jujubae fructus* extract, and *Zingiberis*

*rhizome* extract and a component selected from the group consisting of oxaliplatin, cisplatin, carboplatin, taxol, vincristine, and vinblastine.

* * * * *